(12) United States Patent
Mojaradi

(10) Patent No.: US 8,871,129 B2
(45) Date of Patent: Oct. 28, 2014

(54) BREAST PROSTHESIS

(76) Inventor: Franck Mojaradi, Antibes (FR)

( * ) Notice: Subject to any disclaimer, the term of this patent is extended or adjusted under 35 U.S.C. 154(b) by 219 days.

(21) Appl. No.: 13/485,021

(22) Filed: May 31, 2012

(65) Prior Publication Data

US 2013/0325119 A1 Dec. 5, 2013

(51) Int. Cl.
*A61F 2/12* (2006.01)

(52) U.S. Cl.
USPC ............................ 264/302; 264/301; 623/8

(58) Field of Classification Search
USPC ........................................ 264/301, 302; 623/8
See application file for complete search history.

(56) References Cited

U.S. PATENT DOCUMENTS

| | | | | |
|---|---|---|---|---|
| 5,496,367 A | * | 3/1996 | Fisher | 623/8 |
| 6,383,437 B1 | * | 5/2002 | Grieve | 264/246 |
| 2004/0032056 A1 | * | 2/2004 | Vang et al. | 264/301 |
| 2007/0233273 A1 | * | 10/2007 | Connell | 623/23.72 |
| 2011/0060411 A1 | * | 3/2011 | Govrin-Yehudian et al. | 623/8 |

* cited by examiner

*Primary Examiner* — Larry Thrower
*Assistant Examiner* — Xue Liu
(74) *Attorney, Agent, or Firm* — Renner, Kenner, Greive, Bobak, Taylor & Weber

(57) ABSTRACT

A single opening permanent breast prosthesis includes an envelope made of a flexible, hermatic and biologically inert material having a flat rear surface (3) and a curved front surface (2). The prosthesis thus defines a closed pocket (5) which contains a physiological serum. There are at least two compartments (6, 7, 8) in the pocket (5) which are separated by at least one membrane (10, 11, 12) extending in the form of an arch from the front surface (2) to the rear surface (3) of the prosthesis.

2 Claims, 3 Drawing Sheets

BREAST PROSTHESIS

TECHNICAL FIELD

The present invention relates to a breast prosthesis (or implant) which is permanent or definitive (as opposed to an expansion prosthesis, which is fitted temporarily, and is designed to obtain expansion of the underlying soft tissues), with a single opening (comprising a single large cavity), which in the long term is designed to fill a space in the human body, in particular between the skeleton and the skin.

BACKGROUND ART

A prosthesis of this type comprises an envelope made of a flexible material which is inert from a biological point of view, and in particular is made of silicone, which envelope defines a closed pocket containing in its interior physiological serum consisting of hydrogel or silicone gel with variable cohesiveness. The prosthesis thus has a flexible and malleable nature, which, once it has been fitted, allows it to imitate the appearance and habitual deformations of a natural breast.

The permanent breast prostheses which are sold at present have a major disadvantage, i.e. once they have been fitted, their content (liquid or gel) tends to "drop" downwards and to agglutinate in the lower part of the pocket. Consequently, the upper part of the envelope, on the front side, tends to fold or wrinkle since it is no longer maintained or supported in the interior by the prosthetic content (liquid or gel), as the latter has migrated downwards. The person who is wearing the prosthesis can then have an appearance of folds or "waves", particularly in the top part of the skin of the breast, which firstly is unattractive, and secondly has the effect of indicating to other people that she is wearing a prosthesis.

DISCLOSURE OF THE INVENTION

The objective of the present invention is to overcome the disadvantages of prostheses according to the prior art, and its object is a single-opening permanent prosthesis which, once it has been fitted, does not have folds or wrinkles which can be seen from the exterior, whilst maintaining flexibility and malleability which imitate the breast as perfectly as possible, particularly when palpated.

A median plane is defined, corresponding to the imaginary horizontal plane which divides the prosthetic cavity into two equal, upper and lower volumes in the fitted state.

According to the invention, the single-opening permanent breast prosthesis (or implant) is designed to fill a space in the human body, in particular between the skeleton and the skin.

By thus providing a plurality of compartments in the interior of the breast prosthesis pocket, there is restriction of the possible displacement of the prosthetic content in the smaller compartments, with the result that there is less, or no, migration or agglutination at all of this content towards the bottom of the pocket in the fitted state of the prosthesis; this makes it possible for the implant to retain its form substantially as it was intended by the surgeon, by thus preventing part of the surface of the envelope from folding because there is no longer any gel to support it. This therefore prevents the undesirable folds which, in the case of prostheses according to the prior art, appear once the implant has been put into place. In fact, the compartmentalisation of the single prosthetic cavity means that it is more difficult for the content of the implant to be displaced in the interior of the pocket, and consequently it does not agglutinate, or at least it remains better distributed in the prosthesis when the latter has been fitted. Thus, by means of this direct support action, the front surface is better supported, in particular in its upper part, and maintains a form which is substantially identical to that of a breast. In addition, the structural continuity which is thus created between the front and rear walls of the implant decreases the deformability of the envelope, and therefore its capacity in particular below the median plane, thus creating resistance to agglutination of the prosthetic content in the lower part, and to collapse of the upper part of the envelope because of a lack of direct support, particularly at the level of its front wall. Consequently, the epidermis, and in particular the collagen in the skin of the breast, does not tend to be irremediably deformed by the folds in the prosthesis, once the latter has been fitted.

The present invention also relates to a method for production of a breast prosthesis, in particular a single-opening permanent breast prosthesis or implant, comprising an envelope made of a flexible, hermetic and biologically inert material, which, in the fitted state, has a flat rear surface on the centre of the body side, and a projecting convex front surface on the periphery of the body side, thus imitating the external appearance of a breast, which prosthesis defines a single closed pocket containing physiological serum, consisting of hydrogel or silicone gel or a gel with a silicone base, wherein, in the interior of the single pocket, at least two compartments are defined, which are separated by at least one membrane or partition, the at least one membrane or partition being joined to the envelope and extending from the front surface to the rear surface of the prosthesis, at least once above the median plane defined by the imaginary horizontal plane which, in the fitted state, separates the single pocket of the implant into two equal volumes.

It is thus possible easily to obtain walls in the interior of the prosthesis in order to form compartments, and, at the same time, extraction from the mould of the prosthesis via the hole(s) formed by the presence of the rod(s) for retention during the moulding is facilitated by the fact that, although the secondary elements form for example a complete torus, they can be divided into a plurality of secondary elements, for example quarters of a torus, for their extraction via the hole(s).

Preferably, the detachable securing is obtained by means of magnetisation of the secondary elements, and release by means of de-magnetisation of the secondary elements, for example by activation then deactivation of a magnetic field which is applied to the secondary elements.

BRIEF DESCRIPTION OF THE DRAWINGS

Embodiments of the invention are now represented, provided purely by way of example, with reference to the drawings, in which.

The cross-section

PREFERRED EMBODIMENTS FOR CARRYING OUT THE INVENTION

Figure 1:
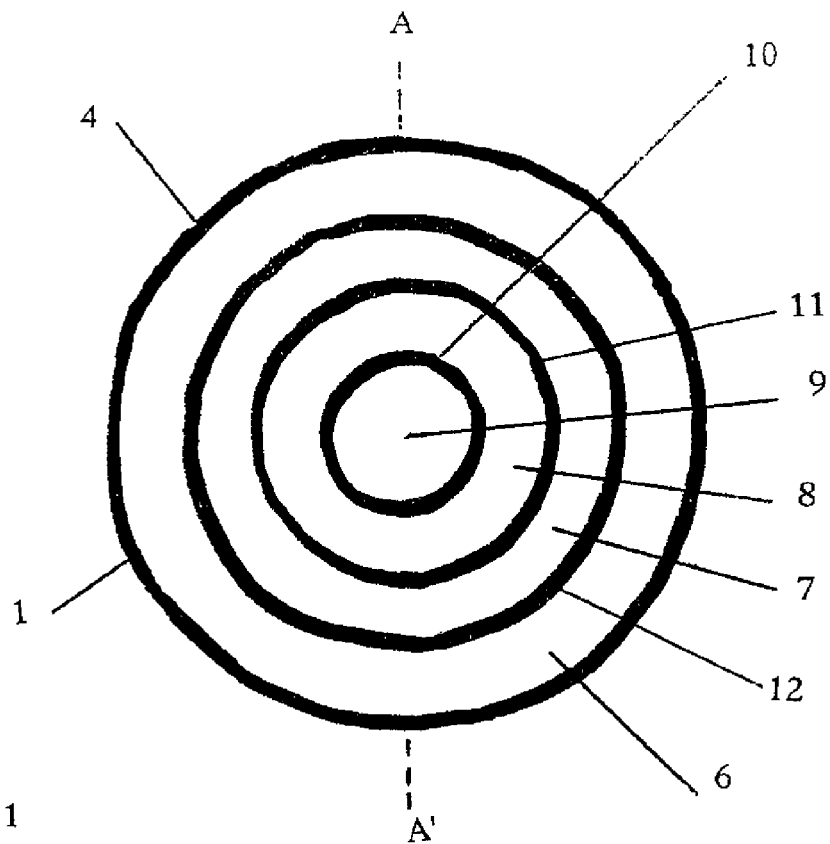
FIG. 1 is a view in cross-section on the frontal plane of a so-called "non-polarised" embodiment of a breast prosthesis according to the invention.
Figure 2:
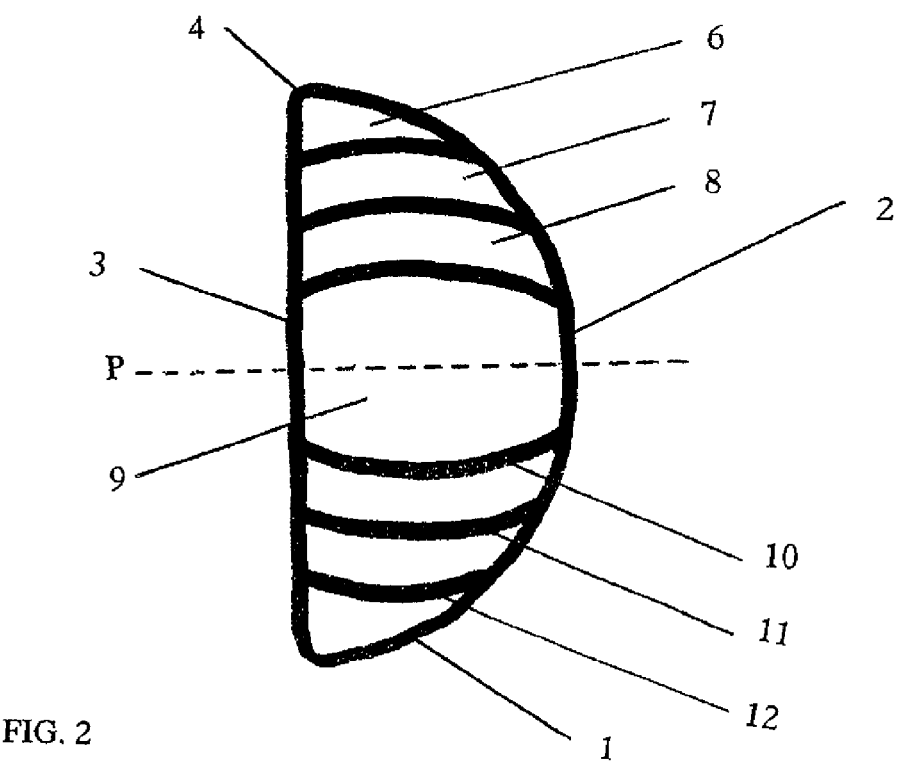
FIG. 2 is a view in cross-section on the median sagittal plane according to the line A-A' in FIG. 1.

FIGS. 1 and 2 represent respectively views in median sagittal and frontal cross-section of a breast prosthesis according to the invention. The prosthesis is constituted by an outer envelope 1 comprising a rear surface 3 which is substantially flat, and is joined to a front surface 2 in the form of a dome along a substantially circular section or edge 4. The inner volume of the envelope 1 defines a pocket 5 filled with physiological serum or gel, which in particular is made of silicone or based on silicone, and is biocompatible but is biologically inert. It will be appreciated that other biocompatible materials could be used.

The lower pocket 5 is subdivided into a plurality of compartments 6, 7, 8 and 9, which are concentric relative to one another. Partitions 10, 11 and 12 in the form of an arch separate the compartments 6, 7, 8 and 9 respectively from one another. Each compartment 6, 7, 8 and 9 is filled with liquid or gel. These compartments can be filled with gels which are identical, or on the other hand with gels with different levels of cohesiveness and/or rheological properties, or with other materials which are more or less liquid.

Each separation wail or separation partition 10, 11 and 12 extends from the flat rear surface 3 of the envelope 1 as far as the convex front surface 2 of the envelope 1. In addition, these partitions are obtained by moulding of the inner sides of the front and rear surfaces of the envelope 1. This is preferable to a prosthesis in which the partitions are secured, for example by means of gluing or thermal welding, to the inner surfaces of the envelope.

However, without departing from the scope of the invention, it would also be possible to secure these partitions to the walls by means of thermal welding or gluing. However, the fact of having the partitions moulded and integral with the front and rear surfaces of the envelope makes it possible to optimise the flexibility of the prosthesis, in particular at the level of the join, whilst retaining the advantage of the prosthesis according to the invention, i.e. of preventing folds from forming once the prosthesis has been fitted. In addition, during handling of the prosthesis and over a period of time, in comparison with a thermal welding or gluing method, the risks of de-insertion of one or more partitions of the envelope are strongly decreased because of the moulding in a single piece.

The thickness of the envelope can in particular be between 100 and 1000 micrometres, whereas the thickness of the or each partition can be between 100 and 2000 micrometres. Preferably, the thickness of the or each partition is equal to, or greater than, the thickness of the envelope.

Figure 3:
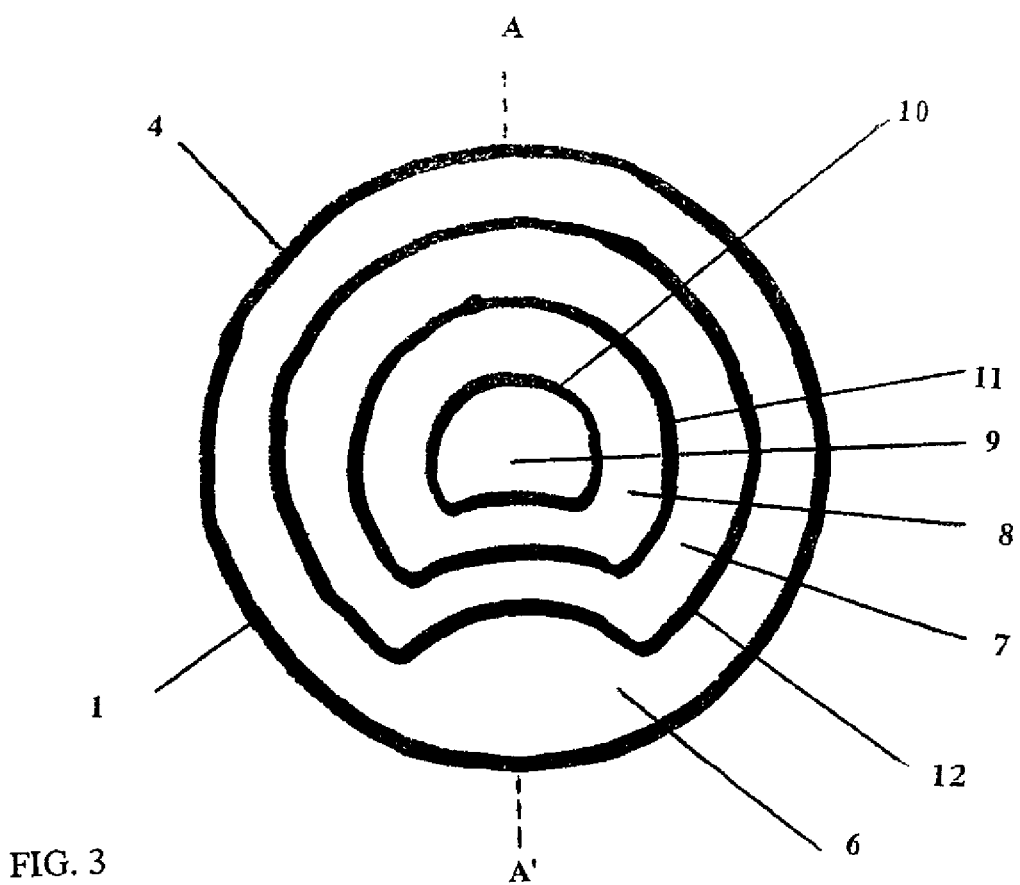
FIG. 3 is a view in cross-section on the frontal plane of another, so-called "polarised" embodiment of a breast prosthesis according to the invention.
Figure 4:
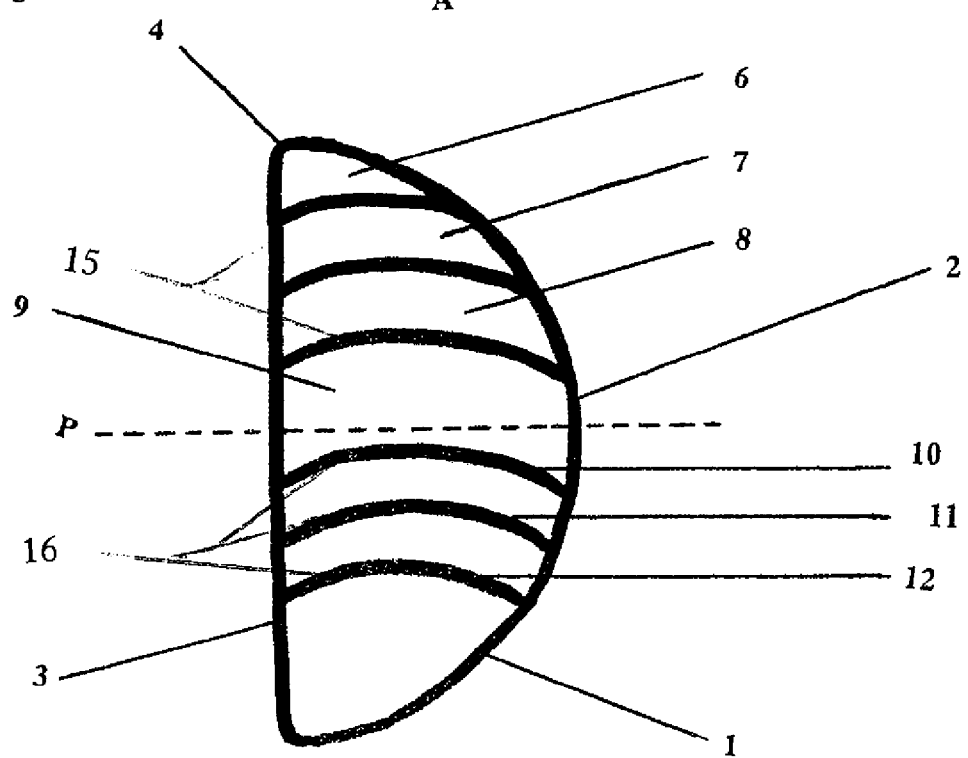
FIG. 4 is a view in cross-section on the median sagittal plane according to the line A-A' in FIG. 3.

FIGS. 3 and 4 represent another embodiment of the invention, which is substantially identical to the embodiment represented in FIGS. 1 and 2. The same numerical references represent the parts which have the same functions. This prosthesis is substantially identical, the only difference being that the prosthesis in FIGS. 3 and 4 is so-called "polarised", i.e. it has a direction of fitting and does not have a symmetrical form relative to a transverse plane other than the median sagittal. In this case, although the partitions 10, 11 and 12 are concentric, when seen in frontal cross-section they do not have a circular form, but have a form as represented in FIG. 3, whilst having a part 15 in the form of an arc of a circle, characterised by a concavity which faces towards the centre of the prosthesis, and a part 16 in the form of an arc of a circle, the concavity of which is inverted relative to the centre of the circle 15. The parts 16 in the form of an arc of a circle are located in the lower part of the pocket 5. In the fitted state of the prosthesis according to the invention, and seen in sagittal cross-section, all the convexities of the partitions are oriented towards the top of the so-called "polarised" version.

Figure 5:
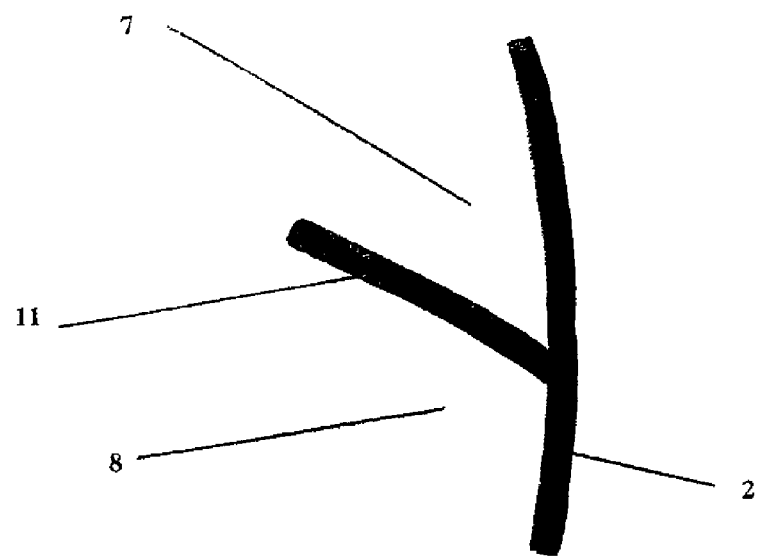
FIG. 5 is a view in enlarged cross-section of the joining of a partition in the form of an arch to the envelope of the prosthesis in FIG. 1.

As can clearly be seen in FIG. 5, the at least one partition is in the form of an arch, and extends from an integrally moulded part of the envelope, from the front wall to the rear wall of the envelope of the prosthesis. This assures the flexibility (with avoidance of rigidifying associated with a thermal welding method, or an excess thickness of materials associated with a gluing process), the solidity and the perennial nature of its insertion.

In order to produce a prosthesis according to the invention, it is possible in particular to use a method by moulding. For example, in order to produce the prosthesis in FIGS. 1 and 2, one takes four (this number is selected according to the number of compartments to be produced) concentric secondary moulding units, which are separated from one another by annular slots, the thickness of which corresponds to that of the future separation membranes or partitions, and have a complementary form which is the negative of the partitions 10, 11 and 12 to be formed in the interior, and each of the secondary units of the main unit (the secondary units correspond to the future compartments 6, 7, 8 and 9) are retained by a respective introduction rod. Each secondary unit comprises at least two secondary elements, for example in the form of a half-torus, which are rendered integral with one another by magnetisation, for example by application of a magnetic field. The four secondary units, each held by their respective introduction rod, are then introduced as many times as necessary into a liquid silicone bath, so that the silicone coats the assembly of the units and fills the slots which are formed between them, the assembly is removed from the bath and the silicone is allowed to dry, the rods are removed, and an annular incision is made, in order then to discard the skin thus formed at the level of the openings left by the rods, so as to extract the secondary elements from the moulding secondary units, separated by de-magnetisation, for example by stopping the magnetic field previously applied, and the final envelope is obtained with the compartments formed in its interior, which each communicate with the exterior by means of an opening corresponding to the passage of the respective grasping rod of the secondary units.

Figure 6:
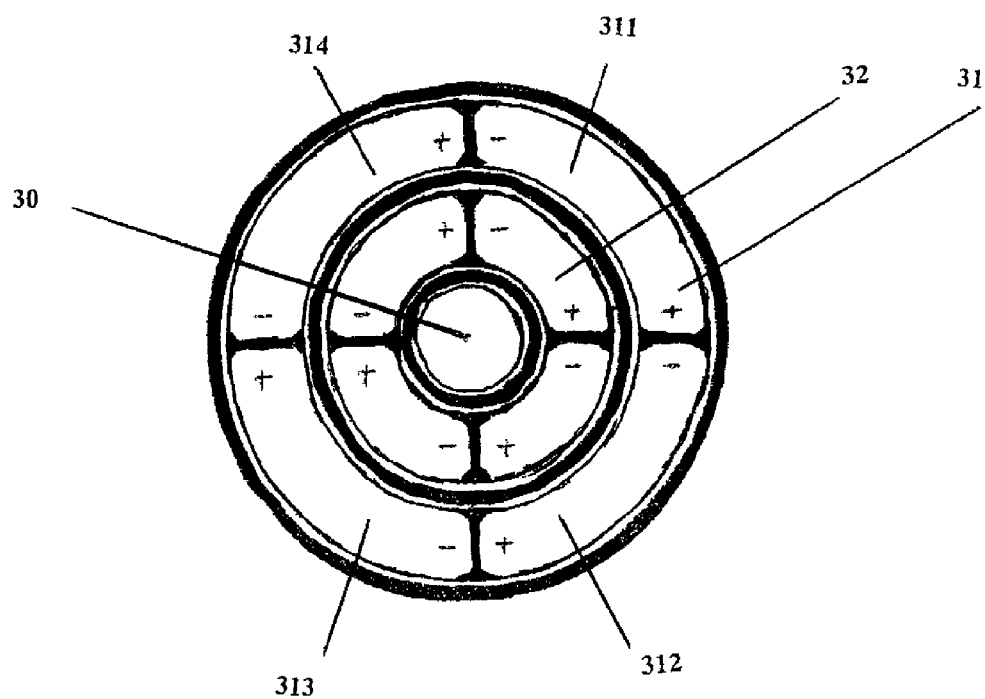
FIG. 6 is a view in cross-section on the frontal plane of an advantageous and original embodiment of a mould comprising various secondary elements which are designed for production of a prosthesis according to the invention.

An advantageous and original production method for obtaining a breast prosthesis according to the invention is represented in FIG. 6. This describes a mould constituted by a central core 30 in the form of a half-sphere, surrounded by toric parts 31, 32 which are concentric relative to the centre of the central core. Each toric part is constituted by four secondary elements 311, 312, 313, 314, which each extend over 90° and which, when placed end to end as in FIG. 6, form a torus which extends around 360°. Each secondary element is pre-magnetised according to a polarity such that the four elements attract one another in order to form the complete torus when they are subjected to a magnetic field.

A description has been given of division of the toruses into four quarters of a torus, in order to facilitate their extraction from the material. However, more or fewer secondary elements of this type could be provided, for example eight, or on the other hand only two, with the original principle of the division and adhesion to one another by magnetisations, then their separation by de-magnetisation, remaining identical.

Thus, after magnetisation, a mould constituted by a plurality of concentric toruses and a central core is obtained, which are each maintained in position by rods. The moulding material is then poured so that the material surrounds the mould entirely (with the exception of the points where the support rods pass), by passing into the gaps between the toruses and the central core. Once the moulding has been completed and drying has taken place, the support rods are removed, then the magnetic field is stopped, so that the secondary elements at 90° can easily be detached, and can each be removed independently from the others by passing through the hole left in the rear wall of the prosthesis by the presence of the rods during the moulding. Since these secondary elements are four times smaller than a complete torus, they can easily pass through the corresponding holes left in the rear wall of the prosthesis.

At this stage it is possible to pierce one or more of the partitions with one or more holes in order to permit restricted passage of the liquid or gel from one compartment to another, for the purpose of improving further the flexibility and malleability of the breast implant when palpated.

Then, the holes in the rear wall of the envelope are closed at the level of each compartment, for example by means of thermally welded patches; this is carried out in a manner which is well known in the field, and in particular in the same manner as that according to which the single compartment of the prostheses which only have a single compartment is now sealed. Then, each compartment is filled with liquid or gel, in particular made of silicone or with a silicone base, with the cohesiveness required for each compartment. The venting of the residual air bubbles and closure of the filling apertures is then obtained according to the usual methods, and according to one of the various options which exist.

What is claimed is:

1. A method for production of a breast prosthesis, characterised in that it consists of forming a mould around which biocompatible and biologically inert moulding material will be poured, the mould being constituted by a central core and at least one element which is retained by a central core and at least one element which is retained by at least one rod in the mould, the said at least one element, being constituted by at least two secondary elements, which are secured to one another in order to form the said at least one element in a detachable manner, pouring the moulding material around the mould which is retained by the said at least one rod, whilst the at least two secondary elements are secured to one another, then releasing the secondary elements from one another and extracting them one after another via the hole(s) created in the rear surface of the prosthesis by the presence of the rod(s).

2. The method according to claim 1, characterised in that the detachable securing is obtained by magnetisation of the secondary elements and release of the secondary elements by de-magnetisation, by activation then de-activation of a magnetic field applied to the secondary elements.

* * * * *